(12) United States Patent
Reynaud et al.

(10) Patent No.: US 9,244,019 B2
(45) Date of Patent: Jan. 26, 2016

(54) METHOD FOR MEASURING DEFECTS IN A SILICON SUBSTRATE BY APPLYING A HEAT TREATMENT WHICH CONSOLIDATES AND ENLARGES THE DEFECTS

(75) Inventors: Patrick Reynaud, Murianette (FR); Christophe Gourdel, Saint Maximin (FR)

(73) Assignee: SOITEC, Bernin (FR)

(*) Notice: Subject to any disclaimer, the term of this patent is extended or adjusted under 35 U.S.C. 154(b) by 571 days.

(21) Appl. No.: 13/547,763

(22) Filed: Jul. 12, 2012

(65) Prior Publication Data
US 2013/0045583 A1 Feb. 21, 2013

(30) Foreign Application Priority Data
Jul. 13, 2011 (FR) .................................... 11 56380

(51) Int. Cl.
*C30B 33/02* (2006.01)
*G01N 21/95* (2006.01)
*H01L 21/66* (2006.01)
*H01L 21/265* (2006.01)
*H01L 21/322* (2006.01)
(Continued)

(52) U.S. Cl.
CPC ...... *G01N 21/9501* (2013.01); *H01L 21/26533* (2013.01); *H01L 21/3226* (2013.01); *H01L 22/12* (2013.01); *H01L 22/24* (2013.01); *G01N 1/28* (2013.01); *G01N 21/4795* (2013.01)

(58) Field of Classification Search
CPC .............. C30B 1/00; C30B 1/02; C30B 1/10; C30B 15/00; C30B 15/14; C30B 33/00; C30B 33/02; H01L 21/02002; H01L 21/02038; H01L 21/02104; H01L 21/02107; H01L 21/30; H01L 21/3226; H01L 21/70; H01L 21/762

USPC .................. 117/2–3, 11, 13–15, 19–20, 928, 117/931–932
See application file for complete search history.

(56) References Cited

U.S. PATENT DOCUMENTS

| 4,324,586 | A | * | 4/1982 | Sasaki | ...................... B01J 27/30 423/510 |
| 4,437,922 | A | | 3/1984 | Bischoff et al. | ............... 156/603 |
| 5,485,803 | A | * | 1/1996 | Habu | ...................... C30B 33/00 117/14 |

(Continued)

OTHER PUBLICATIONS

Hu, S.M. "Growth Law for Disc Precipitates, and Oxygen Precipitation in Silicon", Applied Physics Letters, vol. 48, No. 2, pp. 115-117 (1986).

(Continued)

*Primary Examiner* — Kenneth A Bratland, Jr.
(74) *Attorney, Agent, or Firm* — TraskBritt (57) ABSTRACT

A method for measuring defects in a silicon substrate obtained by silicon ingot pulling, wherein the defects have a size of less than 20 nm. The method includes applying a first defect consolidation heat treatment to the substrate at a temperature of between 750° C. and 850° C. for a time period of between 30 minutes and 1 hour to consolidate the defects; applying a second defect enlargement heat treatment to the substrate at a temperature of between 900° C. and 1000° C. for a time period of between 1 hour and 10 hour hours to enlarge the defects to a size of greater than or equal to 20 nm, with the enlarged defects containing oxygen precipitates; measuring size and density of the enlarged defects in a surface layer of the substrate; and calculating the initial size of the defects on the basis of the measurements of the enlarged defects.

8 Claims, 3 Drawing Sheets

(51) Int. Cl.
  *G01N 1/28* (2006.01)
  *G01N 21/47* (2006.01)

(56) References Cited

U.S. PATENT DOCUMENTS

| | | | | |
|---|---|---|---|---|
| 5,961,713 A | * | 10/1999 | Wijaranakula | C30B 29/06 117/2 |
| 2005/0130394 A1 | | 6/2005 | Falster | 438/480 |
| 2006/0266278 A1 | | 11/2006 | Ono et al. | 117/19 |
| 2007/0231932 A1 | * | 10/2007 | Reynaud | C30B 29/06 438/14 |
| 2011/0084366 A1 | | 4/2011 | Nakai et al. | 257/629 |

OTHER PUBLICATIONS

French Search Report FR 1156380, dated Jan. 31, 2012.

A.-J. Auberton-Hervé et al., "Smart Cut Technology: Industrial Status of SOI Wafer Production and New Material Developments", Electrochemical Society Proceedings vol. 99-3, pp. 93-106, XP009140625, (1999).

* cited by examiner

METHOD FOR MEASURING DEFECTS IN A SILICON SUBSTRATE BY APPLYING A HEAT TREATMENT WHICH CONSOLIDATES AND ENLARGES THE DEFECTS

CROSS-REFERENCE TO RELATED APPLICATION

This application claims priority to French Patent Application Serial No. FR 1156380 filed Jun. 13, 2011, the disclosure of which is hereby incorporated herein in its entirety by this reference.

TECHNICAL FIELD

The present disclosure relates to a method for measuring defects in a silicon substrate, the defects having been present in the substrate since the silicon pulling and having a size of less than 20 nm, as well as to the use of this method for the selection of a suitable substrate with a view to transferring a layer of the substrate in order to form a silicon on insulator (SOI) substrate having an ultrathin active layer.

BACKGROUND

The emergence of substrates of the FDSOI ("Fully Depleted Silicon On Insulator") type has given rise to new problems relating to the crystal quality of the silicon substrates from which they are produced.

Figure 1:
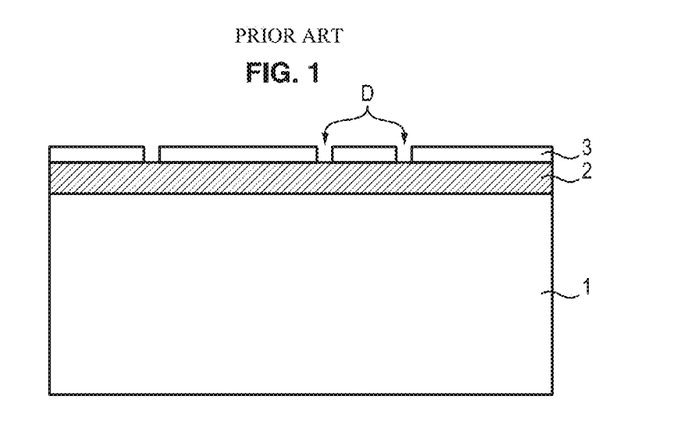
FIG. 1 is a cross-sectional view of a conventional FDSOI substrate comprising through-defects.

FIG. 1 schematically illustrates a section of an FDSOI substrate.

Such a substrate successively comprises a handle substrate 1, a buried oxide layer 2 (often referred to by the acronym BOX for "Buried Oxide") and an ultrathin layer 3 of monocrystalline silicon, which is the active layer, that is to say, in or on which electronic components are intended to be formed.

In the present text, the term "ultrathin" is intended to mean that the thickness of the silicon layer 3 is less than or equal to 20 nm.

The term "FDSOI" refers to an advantageous use of this type of substrate, namely microprocessors. This is because the great thinness of the active layer and, where applicable, the oxide layer, allow the active layer of a transistor formed from this substrate to be fully depleted.

Such a substrate is advantageously, but not exclusively, produced by a method of the SMARTCUT® type, which typically comprises provision of the handle substrate and of a donor substrate from which the active layer will be transferred, the formation of an oxide layer on the surface of the handle substrate and/or of the donor substrate, the formation of a weakened zone in the donor substrate so as to delimit the layer to be transferred, bonding of the substrates via the oxide layer(s), which form the buried oxide, then cleavage of the donor substrate along the weakened zone.

For the formation of FDSOI substrates, donor substrates having an excellent crystal quality are selected.

To this end, donor substrates are selected that are cut from silicon ingots produced according to the NPC ("Near Perfect Crystal") process, which is the one that generates the fewest defects in the silicon. Donor substrates cut from silicon ingots produced according to the NPC process are used as donor substrates for the production of SOIs for which the active silicon layer has a thickness of 50 nm or more, without introducing an excessive number of defects into this layer.

After cleavage of the donor substrate, however, the active silicon layer 3 may comprise through-defects (holes) D that open into the buried oxide layer 2.

These through-defects are due to defects that were originally present in the silicon ingot from which the donor substrate was formed, and that have a size of between 1 and 20 nm.

Owing to the extreme thinness of the silicon layer, these original defects have a size sufficiently large to pass through the active layer 3, even though they do not affect the silicon layer of a "conventional" SOI substrate, the thickness of which is much greater (of the order of 80 to 100 nm, for example).

These original defects are to be distinguished from oxygen precipitates, from which they differ both morphologically and dimensionally.

Figure 2:
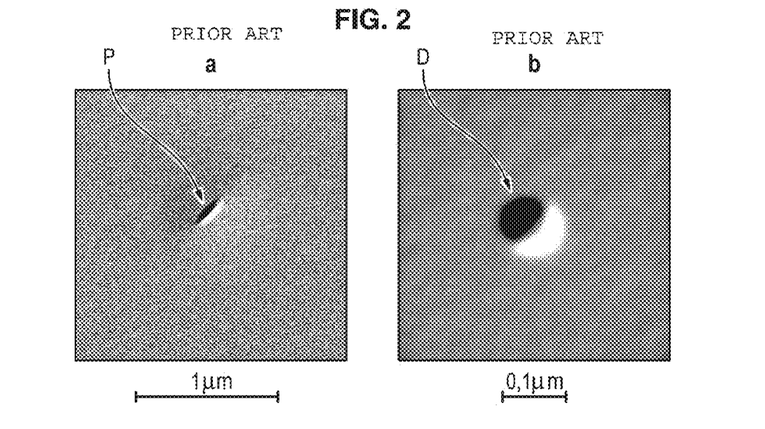
FIG. 2 presents photographs of an oxygen precipitate (Panel a) and an original defect of the silicon (Panel b), which can exist in silicon material and which defects can be measured by the present disclosure.

For instance, FIG. 2 Panel a presents a photograph of an oxygen precipitate P and FIG. 2 Panel b presents a photograph of an aforementioned original defect D.

In both cases, these SEM ("Scanning Electron Microscopy") photographs were taken from an FDSOI substrate, the thickness of whose active silicon layer 3 is 12 nm.

Thus, while the oxygen precipitate P has an elongate shape and a length of about 0.2 µm, the original defect D of the silicon has a round shape with a diameter of about 0.08 µm.

Unlike known oxygen precipitates that are generated during heat treatments of a silicon substrate, these original defects are generated during the pulling of the silicon ingot, and they exist therein before any application of a heat treatment.

It should be pointed out that, in the present text, the term "heat treatment" means the introduction of a silicon wafer into a furnace in order to heat it to a high temperature.

During the pulling of the ingot, the silicon is in the liquid state, that is to say, at a temperature above 1,414° C. (melting temperature of silicon), and it cools from 1,414° C. to room temperature when drawn to form an ingot in air, but these steps of producing the silicon ingot are not heat treatments in the sense intended here.

Although the origin of these defects is not precisely known, the current hypothesis is that they are formed during the cooling of the silicon ingot by coalescence of voids, possibly including the creation of an oxygen precipitate inside each void.

The presence of the through-defects D in the active layer 3 (that is to say, a localized absence of silicon) is intolerable because a chip produced on such a defect would be defective.

Even though the heat treatments applied to the silicon when carrying out the SMARTCUT® method probably have the effect of enlarging these defects, these defects would be critical even in the absence of any heat treatment. These defects are difficult to locate because the size of the original defects of the silicon is less than the current detection limit of measurement equipment present on the market, which is on the order of 20 nm. There is, therefore, currently no method for identifying the presence or absence of these defects in a donor substrate, or for measuring the size and the density of these defects, before carrying out the SMARTCUT® method. Thus, there is a need for such method and this is now provided by the present disclosure

BRIEF SUMMARY

This disclosure now defines a method for measuring, in a silicon substrate, defects that have been present in the substrate caused by silicon ingot pulling, the defects being the size of less than 20 nm. This method is useful for selecting a silicon donor substrate with a view to carry out the SMART- Cut® method thereon in order to produce an SOI substrate in which the active layer transferred from the donor substrate is ultrathin.

The disclosed method is thus for measuring defects in a silicon substrate obtained by silicon ingot pulling, wherein the defects have a size of less than 20 nm. This method includes applying a first defect consolidation heat treatment to the substrate at a temperature of between 750° C. and 850° C. for a time period of between 30 minutes and 1 hour to consolidate the defects; applying a second defect enlargement heat treatment to the substrate at a temperature of between 900 and 1,000° C. for a time period of between 1 hour and 10 hours to enlarge the defects to a size of greater than or equal to 20 nm, with the enlarged defects containing oxygen precipitates; measuring size and density of the enlarged defects in a surface layer of the substrate; and calculating the initial size of the defects on the basis of the measurements of the enlarged defects.

The measuring of the size and density of the enlarged defects is preferably conducted with a measurement device having a resolution that is finer than the size of the enlarged defects, such as light scattering tomography equipment. Also, the surface layer of the substrate wherein the measurements are taken has a thickness of less than or equal to 50 μm.

The initial size of the defects is calculated by measuring the average size of the enlarged defects by light scattering tomography after the second heat treatment, calculating a radius of an expanded sphere equivalent to the volume of the oxygen precipitate contained in the enlarged defect after the second heat treatment is completed, calculating the radius of an initial sphere equivalent to an oxygen precipitate contained in the initial defect on the basis of the radius, and then calculating the initial size of the defect on the basis of the calculated radius of the initial sphere. These calculations are preferably made using a processing device.

Another embodiment of the disclosure relates to a method for selecting a silicon substrate for transferring an active silicon layer having a thickness of less than or equal to 20 nm from the substrate in order to produce a silicon on insulator substrate. This method comprises conducting the defect measuring method described herein on a reference substrate obtained from an ingot that is the same ingot as the silicon substrate to be selected in order to measure defects present therein, and selects the substrate if the initial size of the defects of the reference substrate is less than 5 nm and their density is less than $10^7$ defects/cm$^3$ in the surface layer of the reference substrate. The method preferably also measures holes or scratches on the surface of the reference substrate, and selects the substrate when the size of the holes or scratches is less than 6 nm in the reference substrate.

Yet another embodiment of the disclosure relates to a method for producing a silicon on insulator substrate comprising a handle substrate, a buried oxide layer and an active silicon layer having a thickness of less than or equal to 20 nm, which method comprises selecting a donor substrate according to the selection method described herein; providing a handle substrate; forming an oxide layer on a surface of the handle substrate, a surface of the donor substrate, or on both surfaces; forming a weakened zone delimiting a layer intended to form the active layer to be transferred from the donor substrate; bonding the donor and handle substrates together with the oxide layer(s) therebetween at an interface in order to form a buried oxide layer; and breaking the donor substrate along the weakened zone to transfer the active layer to the handle substrate. The weakened zone is typically produced by introducing or implanting atomic species into the donor substrate.

Also, the disclosure relates to a system for carrying out the methods described herein. This system comprises a device for measuring the size and the density of the enlarged defects in the surface layer of the silicon substrate and a processing device operatively associated with the measuring device, and adapted to calculate the initial size of the defects on the basis of the measurements of the size of the enlarged defects. The preferred measurement device is a light scattering tomography device.

BRIEF DESCRIPTION OF THE DRAWINGS

Other characteristics and advantages of the disclosure will emerge from the following detailed description with reference to the appended drawings, in which.

For reasons of clarity in the figures, the respective thicknesses of the various layers have not necessarily been represented on their true scale in the diagrams.

DETAILED DESCRIPTION

The disclosure specifically provides a method for measuring defects in a silicon substrate, the defects having been present in the substrate since the silicon pulling and having a size of less than 20 nm, the method being characterized in that it comprises the following steps:

(i) applying a first heat treatment (called "defect consolidation") to the substrate at a temperature of between 750° C. and 850° C. for a time period of between 30 minutes and 1 hour;

(ii) applying a second heat treatment (called "defect enlargement") to the substrate at a temperature of between 900° C. and 1,000° C. for a time period of between 1 hour and 10 hours, the heat treatment leading to enlargement of the defects to a size of greater than or equal to 20 nm, the enlarged defects containing an oxygen precipitate;

(iii) measuring the size and the density of the enlarged defects in a surface layer of the substrate by means of a measurement device having a resolution finer than the size of the enlarged defects;

(iv) calculating the initial size of the defects on the basis of the measurements.

In the present text, the term "size" is intended to mean the largest dimension of an object. When the object is of substantially circular or spherical shape, its size corresponds to the diameter of the circle or sphere.

Particularly advantageous, the surface layer in which the size and the density of the enlarged defects are measured has a thickness of less than or equal to 50 μm.

The size and the density of the enlarged defects are preferably measured by light scattering tomography.

According to a preferred embodiment of the disclosure, the following steps are carried out in order to calculate the initial size of the defects:
 (i) the average size of the enlarged defects is measured by light scattering tomography at the end of the second heat treatment;
 (ii) the radius of the sphere equivalent to the volume of the oxygen precipitate contained in the enlarged defect after the heat treatment is calculated;
 (iii) the radius of a sphere equivalent to an oxygen precipitate contained in the initial defect is calculated on the basis of the radius;
 (iv) then the initial size of the defect is calculated on the basis of the radius.

Another object of the disclosure relates to a method for selecting a silicon substrate with a view to transferring a silicon layer from the reference substrate in order to produce a silicon on insulator substrate, the active silicon layer of which has a thickness of less than or equal to 20 nm, wherein:
 the measurement method described above is carried out on a reference substrate obtained from the same ingot as the silicon substrate to be selected, in order to measure the defects that have been present in the reference substrate since the pulling of the silicon and have a size of less than 20 nm; and
 the substrate is selected if the initial size of the defects of the reference substrate is less than 5 nm and their density is less than $10^7$ defects/$cm^3$ in the surface layer of the reference substrate.

Preferably, the holes and/or scratches present on the surface of the silicon substrate are furthermore measured, and a substrate in which the size of the holes and/or scratches is less than 6 nm is selected.

The disclosure also relates to a method for producing a silicon on insulator substrate comprising a handle substrate, a buried oxide layer and an active silicon layer having a thickness of less than or equal to 20 nm, the method comprising the steps of:
 providing the handle substrate and a donor substrate of silicon;
 forming an oxide layer on the surface of the handle substrate and/or of the donor substrate;
 forming a weakened zone, delimiting a layer intended to form the active layer, in the donor substrate;
 bonding the donor substrate and the handle substrate, the oxide layer(s) being at the interface and forming the buried oxide layer; and
 breaking the donor substrate along the weakened zone.
This method is characterized in that the donor substrate is selected according to the selection method described herein.

Preferably, the weakened zone is produced by introducing atomic species into the donor substrate.

Lastly, the disclosure relates to a system for carrying out the measurement method described above, characterized in that it comprises:
 a device for measuring the size and the density of the enlarged defects in a surface layer of the silicon substrate;
 a processing device adapted to calculate the initial size of the defects on the basis of the measurements of the size of the enlarged defects.

Particularly advantageous, the measurement device is a light scattering tomography device.

The various steps of the defect measurement method according to the disclosure will now be described.

The starting point is a substrate (wafer) of monocrystalline silicon on which the size and density of the original defects are intended to be measured. This substrate typically has a thickness of 775 μm+/−25 μm.

It is assumed that a determination of the size and the density of the original defects on a substrate obtained from an ingot gives a reliable indication of the size and of the density of the defects in the other substrates cut from this ingot. The substrates may be classed as "good" or "poor" according to the size and the density of the measured defects, it being understood that "poor" substrates may be used as donor substrates for the transfer of a silicon layer of greater thickness, for example, more than 50 nm.

Heat Treatments for Consolidation and Enlargement of the Defects

Since the original defects are too small to be detected by the inspection means currently available on the market, it is necessary to apply a heat treatment to the substrate in order to enlarge them. This heat treatment is difficult to carry out, however, because it requires only enlargement of the original defects without generation of new defects (for example, oxygen precipitates). Furthermore, the original defects are very unstable defects that may be dissolved under the effect of a heat treatment at high temperature (that is to say, typically above 1,000° C.).

It is, nevertheless, necessary to apply a sufficiently high temperature so that the defects D grow until they reach a size of greater than or equal to 20 nm, which will be detectable by the inspection means. This is because if the heat treatment is applied at a temperature lower than approximately 750° C., the size of the defects will remain less than 20 nm so that the defects are not detectable.

The disclosure provides a heat treatment in two phases. A first phase, called a "consolidation phase," is intended to make the defect grow slightly without dissolving it. This is because the enlarged defect subsequently has less risk of being dissolved during the application of a heat treatment at a high temperature. The consolidation phase, therefore, advantageously comprises the application of a temperature plateau at a temperature of between 750° C. and 850° C., preferably about 800° C., for a time period of between 30 minutes and 1 hour.

A second phase, called "enlargement," is intended to make the consolidated defect grow. This second phase is carried out at a temperature higher than that of the first phase, while remaining lower than a temperature of about 1,000° C. above which the defect would risk being dissolved despite being consolidated in the first consolidation phase. The second phase typically comprises the application of a temperature of between 900° C. and 1,000° C. for a time period of from 1 to 10 hours. The higher the treatment temperature of this second phase is, the more rapidly the defects grow and the shorter the duration of this phase is. Advantageously, the second phase is carried out at 900° C. for 6 hours.

The second phase may follow the first phase directly, that is to say, the substrate remains in the same furnace and the temperature is raised at the end of the first phase to the temperature of the second phase. This option is advantageous in industrial terms since it is shorter. Alternatively, the first and second phases may be separated by a certain time lapse, comprising, for example, removal of the substrate from the furnace at the end of the first phase, cooling it to room temperature, then reintroduction into the furnace in order to carry out the second phase.

During the first and second phases, the atmosphere of the furnace is preferably nitrogen and/or argon. This type of heat treatment is called an "anneal" in the terminology of the art.

Optionally, the atmosphere may also comprise a small proportion of oxygen (for example, between 10 and 25 sscm). This is called a "wet ox" heat treatment. During this treatment, an oxide layer is formed on the surface of the substrate, and this needs to be removed in order to measure the defects.

Measurement of the Enlarged Defects

Once the defects have been enlarged by means of the two heat treatment phases described above, they will have a size of more than 20 nm, which makes them detectable and measurable by inspection means available on the market. The inspection means, in particular, advantageously comprises light scattering tomography (LST) devices, for example, the device M0601 from Raitex or the device LST-300 from Semilab. The measurement comprises sending a light beam (infrared) onto the substrate by using a laser. The defects generate scattering of the light. A detector at the beam output collects the information (scattered light), which is then converted into defects. The size of the defects can be deduced therefrom as a function of the light intensity at the output.

In the disclosure, the measurement is carried out over a depth of 400 µm across the 775 µm of the width of the wafer, which corresponds to the current limit of existing equipment, but only the information between 0 and 50 µm are filtered and analyzed in the data processing. In other words, only a surface layer of the substrate is taken into account, the thickness of which is of the order of 50 µm, that is to say, the size and density of the enlarged defects are measured only in a region lying between a depth of 0 and 50 µm from the surface of the substrate. This is because for the transfer of the silicon layer during the production of an SOI, only the first 10 micrometers of the donor substrate need to have an excellent quality since only a very fine thickness of silicon is transferred, even in the case of successive transfers from the same substrate. Moreover, the Applicant has observed that it is principally between a depth of 0 and 50 µm that the enlarged defects D' appear (or do not appear), depending on the ingots, and that it is, therefore, this surface layer that is representative for characterizing the original defects.

Figure 3:
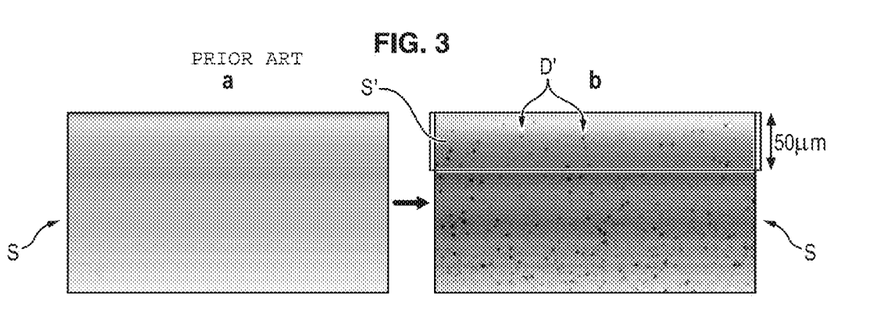
FIG. 3 presents photographs taken by a light scattering tomography device of a silicon substrate before any heat treatment (Panel a) and after a heat treatment carried out in the measurement method according to the disclosure (Panel b)

FIG. 3a is a photograph taken by a light scattering tomography device of a silicon substrate S before any heat treatment; FIG. 3b is a photograph of the same substrate S after the heat treatment for consolidation and enlargement of the defects, as described above. The surface layer in which the enlarged defects are counted and measured is shown by the reference S'. Although no defect is observed in FIG. 3a, a plurality of enlarged defects D' are detected in FIG. 3b, these being presented in the form of dark spots. It is, therefore, possible to count these enlarged defects D' with a view to deducing therefrom their density (expressed as number of defects/cm$^3$). Furthermore, the average size of the largest defects measured is measured in the surface layer S' (for example, the average size of the five largest defects).

Determination of the Initial Radius of the Original Defects on the Basis of the Average Size of the Enlarged Defects At the end of the enlargement treatment, the enlarged defects contain an oxygen precipitate, which it is assumed either may have existed in the defect before the heat treatment and grown with it, or may have been generated during the heat treatment and have come to fill the defect. In any event, the measurement method that is described in detail below is based on:

(1) measuring an oxygen precipitate contained in a defect that has been enlarged by means of the aforementioned heat treatment;
(2) on the basis of this measurement, deducing the initial size of an oxygen precipitate that would have been contained in the original defect and which, under the effect of the enlargement heat treatment, would have given rise to the measured enlarged precipitate;
(3) lastly, reducing the size of the original defect on the basis of the initial size of the precipitate.

The size R of the enlarged defects is connected with the initial size of the original defects (before any heat treatment) by a formula of the type:

$$R^2 = R_i^2 + Kt$$

The following quantities are defined:
R: average size of the enlarged defects (homogeneous with a diameter); this is an arithmetic mean taken over the five largest defects measured $$r_P = R/2$$

r: radius of the sphere equivalent to the volume of the oxygen precipitate contained in the defect D' after heat treatment $r_0$: radius of the sphere equivalent to the volume of an oxygen precipitate that would have been contained in the defect D before any heat treatment and that would have given rise to the oxygen precipitate observed in the enlarged defect D'

$R_i$: size of the defect D before any heat treatment t: duration of the heat treatment The term K t represents the enlargement of the defect, which is a function of time, K being a constant taking into account the three growth parameters of a precipitate, namely the oxygen solubility, the oxygen diffusion and the oxygen concentration in the silicon.

On the basis of the measurement of the average size R of the largest defects, $R = 2 r_P$ is converted into the size 2 r of the sphere equivalent in volume, by using the formula disclosed in Hu (Applied Physics Letters, Vol. 48, No. 2 (1986)):

$$\frac{r_P}{L} = \frac{\left(\frac{3}{4}\frac{r_P^3}{r^3 s}\right)^2}{\ln\left(\frac{3}{4}\frac{r_P^3}{r^3 s}\right) + \ln\left(\frac{8}{e^2}\right)}$$

where s=0.24 and L=0.36 Å.

The formula described by Ham (J. Chem. Phys. Solids, Vol. 6, p. 335 (1958)) may then be employed, which makes it possible to determine the radius $r_0$ of the sphere equivalent to the volume of the precipitate before any heat treatment:

$$r^2(t) = 2 D_{Oi}^{Si}\left(\frac{[Oi] - C_{Ox}^*}{c_P - C_{Ox}^*}\right)t + r_0^2$$

where:

$D_{Oi}^{Si}$ is the diffusion coefficient of the interstitial oxide in silicon, $[O_i]$ is the interstitial oxide concentration, $C^*_{Ox}$ is the solubility of the oxide in silicon, $c_P$ is the oxide concentration in the precipitate ($c_P = 4.4 \times 10^{22}$ at/cm$^3$), and t is the duration of the heat treatment.

In the disclosure, the heat treatment is carried out in two phases: a consolidation changing the radius from $r_0$ to $r_1$ during a time $t_1$, then enlargement changing the radius from $r_i$ to $r_2$ during a time $t_2$. Given r, which is known experimentally by the measurement and which is taken from the Hu formula above, $r_1$ is first determined by the Ham formula written during the enlargement step:

$$r^2 = 2D_{Oi}^{Si}\left(\frac{[Oi] - C_{Ox}^*}{c_P - C_{Ox}^*}\right)t_2 + r_1^2$$

where $D_{Oi}^{si}$ and $C_{Ox}^*$ are evaluated under thermal conditions of the enlargement.

Next, $r_0$ is deduced on the basis of $r_1$ by the Ham formula written during the consolidation step:

$$r_1^2 = 2D_{Oi}^{Si}\left(\frac{[Oi] - C_{Ox}^*}{c_P - C_{Ox}^*}\right)t_1 + r_0^2$$

where, this time, $D_{Oi}^{si}$ and $C_{Ox}^*$ are evaluated under thermal conditions of the consolidation.

Once the radius $r_0$ has been obtained, it remains to apply the Hu formula below in order to determine the initial size $R_i = 2 r_i$ of the defect, the radius $r_i$ of the precipitate being defined by:

$$\frac{r_i}{L} = \frac{\left(\frac{3}{4}\frac{r_i^3}{r_0^3 s}\right)^2}{\ln\left(\frac{3}{4}\frac{r_i^3}{r_0^3 s}\right) + \ln\left(\frac{8}{e^2}\right)}.$$

These various calculation steps are advantageously carried out by a processing device, for example, a computer on which an algorithm containing the formulae for obtaining the value $R_i$ is implemented.

Strategy for Selection of a Substrate for the Production of an SOI Substrate Having an Ultrathin Silicon Layer On the basis of the determination of the density and the initial size of the defects in a substrate originating from an identified ingot, the substrates obtained from the same ingot may be regarded as "good" if, in the substrate on which the determination has been carried out, the size $R_i$ of the defects is less than 5 nm and the density of the defects is less than $10^7$ defects/cm$^3$ in a surface layer having a thickness of 50 micrometers. Such substrates may be used as donor substrates for the transfer of an ultrathin silicon layer onto a handle substrate. This is because even though the heat treatments experienced by the silicon during the production of the SOI involve high temperatures, the defects do not risk growing to the point of reaching a size making them through-defects.

Moreover, for the production of an SOI whose silicon layer has a thickness of less than 20 nm, it is preferable for the donor substrate furthermore to comprise no defect with a size of more than 6 nm. Such defects may be:

- scratches due to the final polishing of the substrate with a view to making it usable as a donor substrate,
- holes generated by the final polishing by the silicon manufacturer (after cutting the ingot), which are due, in particular, to the particles of the slurry that is used for this polishing, or
- residues of metallic contaminants, which may be introduced by the tools handling the substrate during its production or subsequent steps of producing the SOI; these residues may generate "pits" during the heat treatments subsequently applied.

Consequently, the method for selecting a substrate for the production of an SOI substrate having an ultrathin silicon layer may, further to the size and density criteria of the original defects, be based on a criterion according to which the other defects mentioned above have a size (diameter or depth) of less than 6 nm.

Experimental Results

The method described above was carried out on substrates obtained from three different ingots, all three produced according to the NPC process, while substrates obtained from the same ingots were used to produce SOIs having an ultrafine thickness.

Tests have made it possible to compare the results of the method for determining the size and the density of the defects in a substrate with the appearance or lack of appearance of through-defects in an SOI produced from a substrate obtained from the same ingot.

The method of the disclosure was carried out on three substrates $S_A$, $S_B$, $S_C$ obtained from three different ingots A, B, and C. The substrates had a thickness of approximately 400 μm.

Figure 4:
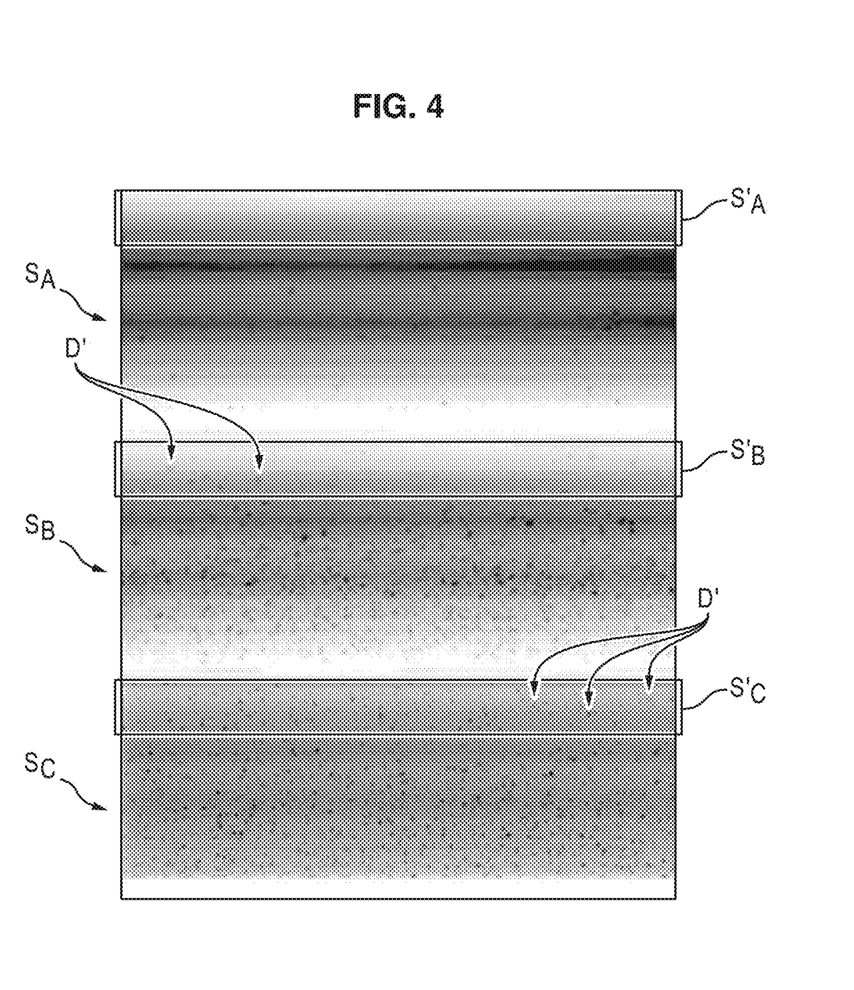
FIG. 4 presents photographs taken by a light scattering tomography device of silicon substrates obtained from three different ingots at the end of a heat treatment carried out in the measurement method according to the disclosure.

FIG. 4 includes photographs taken by a light scattering tomography device of the substrates $S_A$, $S_B$ and $S_C$ at the end of a heat treatment carried out in the measurement method according to the disclosure (the consolidation phase being carried out at 800° C. for 30 minutes and the defect enlargement phase being carried out at 900° C. for 6 hours).

It is observed that the surface layer $S'_A$ of the substrate $S_A$ seems free of defects, while the surface layers $S'_B$ and $S'_C$ of the substrates $S_B$ and $S_C$ have an increasing density of defects D'. In fact, the defect density in the surface layer $S'_A$ of the substrate $S_A$ lies between 0 and $10^7$ defects/cm$^3$ and their size $R_i$ is less than 5 nm, which is considered to be acceptable for the production of an SOI having an ultrathin silicon layer.

An SOI substrate produced from a substrate obtained from ingot A did not give rise to through-defects. Conversely, the defect density in the surface layer $S'_B$ of the substrate $S_B$ lies between $10^7$ and $10^8$ defects/cm$^3$ and their size $R_i$ lies between 5 and 10 nm, while the defect density in the surface layer $S'_C$ of the substrate $S_C$ is more than $10^8$ defects/cm$^3$ and their size $R_i$ lies between 10 and 20 nm.

The substrates obtained from ingots B and C, therefore, give rise to the formation of through-defects during the production of an SOI having an ultrathin silicon layer. On the other hand, these substrates can be used without risk for the production of an SOI whose silicon layer has a thickness of more than 50 nm.

Production of an SOI by the SMARTCUT® Method

Figure 5A:
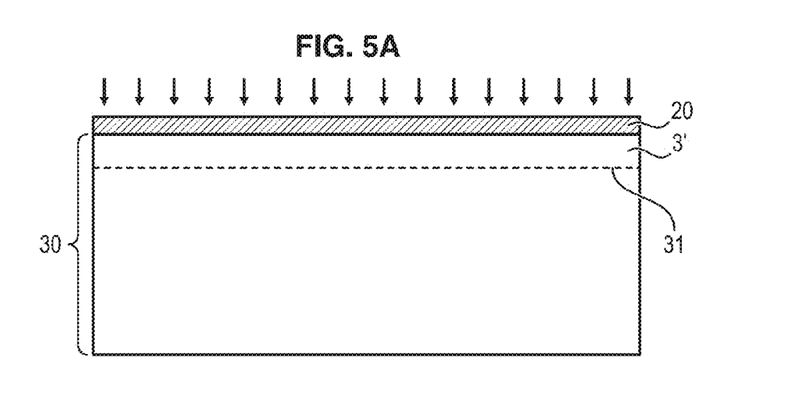
FIGS. 5A to 5C illustrate the main steps carried out in the production of a semiconductor on insulator substrate by a SmartCut® method.
Figure 5B:
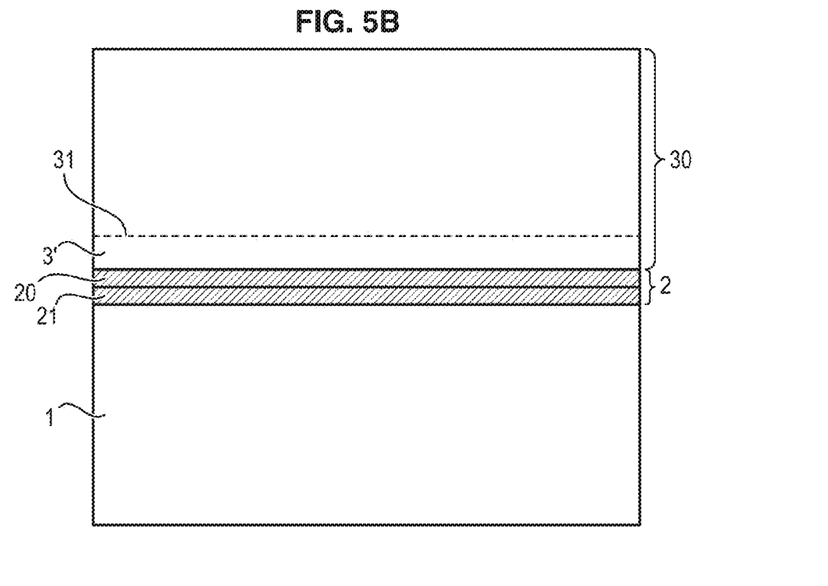
Figure 5C:
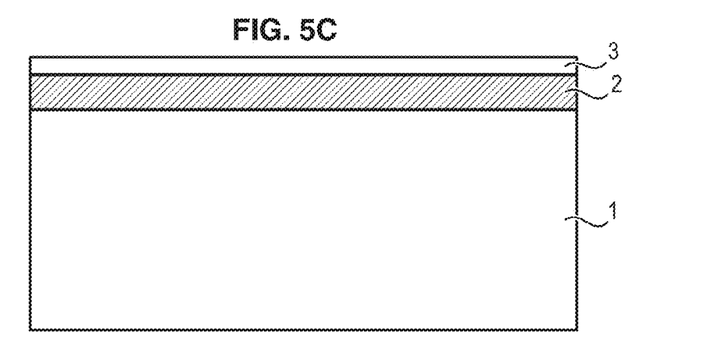

FIGS. 5A to 5C depict various steps in the production of an SOI by a layer transfer method of the SMARTCUT® type.

Referring to FIG. 5A, a donor substrate 30 of silicon selected according to the method described above is provided, that is to say, one in which the density of original defects is less than $10^7$ defects/cm$^3$ and in which the initial size of the defects is less than 5 nm.

An oxide layer 20 is formed on the donor substrate 30. Implantation of atomic species (for example hydrogen and/or helium) is then carried out through the oxide layer 20. The implantation makes it possible to form a weakened zone 31, which delimits the layer 3' to be transferred in order to produce the active layer 3 of the SOI, in the donor substrate 30. Alternatively, any other technique of introducing species into the donor substrate may be employed, for example, diffusion of species from the surface of the donor substrate.

Because of the treatments that will be applied to the active layer after breaking (polishing, smoothing, etc.), the transferred layer 3' is thicker than the final active layer 3. For example, if the active layer 3 is intended to have a final thickness of 12 nm, the layer 3' transferred from the donor substrate 30 will have a thickness of the order of 200 nm.

Referring to FIG. 5B, the donor substrate 30 weakened in this way is bonded onto a handle substrate 1. The handle substrate 1 is optionally covered with an oxide layer 21, in which case, the oxide layers 20 and 21 together form the buried oxide layer 2 of the SOI. The donor substrate 30 is then broken or fractured along the weakened or embrittled zone 31, which leads to the silicon layer 3' being transferred onto the handle substrate 1.

Referring to FIG. 5C, the necessary treatments of polishing, smoothing, defect annealing, etc., are carried out on the transferred layer 3', which leads to it being thinned in order to obtain the final active layer 3 whose thickness is less than 20 nm. The SOI substrate formed in this way does not have through-defects in the active layer and can, therefore, be used for the production of electronic, optical, optoelectronic components, etc.

What is claimed is:

1. A method for measuring defects in a silicon substrate obtained by silicon ingot pulling, wherein the defects have a size of less than 20 nm, the method comprising:
    applying a first defect consolidation heat treatment to the silicon substrate at a temperature of between 750° C. and 850° C. for a time period of between 30 minutes and 1 hour to consolidate defects having a size of less than 20 nm in the silicon substrate, under an atmosphere consisting of at least one of argon and nitrogen, without generating additional defects;
    applying a second defect enlargement heat treatment to the silicon substrate at a temperature of between 900° C. and 1,000° C. for a time period of between 1 hour and 10 hours to enlarge the defects having a size of less than 20 nm in the silicon substrate to a size of greater than or equal to 20 nm, with the enlarged defects containing oxygen precipitates, under an atmosphere consisting of at least one of argon and nitrogen, without generating additional defects;
    measuring size and density of the enlarged defects in a surface layer of the silicon substrate; and
    calculating the initial size of the defects on the basis of the measurements of the enlarged defects;
    wherein the silicon substrate is maintained at temperatures at or below 1,000° C. throughout the first defect consolidation heat treatment and the second defect enlargement heat treatment.

2. The method according to claim 1, wherein the measuring of the size and density of the enlarged defects is conducted with a measurement device having a resolution that is finer than the size of the enlarged defects.

3. The method according to claim 1, wherein the surface layer of the silicon substrate wherein the measurements are taken has a thickness of less than or equal to 50 μm.

4. The method according to claim 1, wherein the size and the density of the enlarged defects are measured by light scattering tomography.

5. The method according to claim 1, wherein the initial size of the defects is calculated by:
    measuring the average size of the enlarged defects by light scattering tomography after the second defect enlargement heat treatment;
    calculating a radius of an expanded sphere equivalent to the volume of the oxygen precipitate contained in the enlarged defect after the second defect enlargement heat treatment is completed;
    calculating the radius of an initial sphere equivalent to an oxygen precipitate contained in the initial defect on the basis of the radius; and
    then calculating the initial size of the defect on the basis of the calculated radius of the initial sphere.

6. The method according to claim 5, wherein the calculations are made using a processing device.

7. A method for selecting a silicon substrate for transferring an active silicon layer having a thickness of less than or equal to 20 nm from the silicon substrate in order to produce a silicon on insulator substrate, which comprises:
    conducting the method according to claim 1 on a reference substrate obtained from an ingot, which is the same ingot as the silicon substrate to be selected, in order to measure defects present therein; and
    selecting the silicon substrate selected if the initial size of the defects of the reference substrate is less than 5 nm and their density is less than $10^7$ defects/cm$^3$ in the surface layer of the reference substrate.

8. The method according to claim 7, which further comprises measuring holes or scratches on the surface of the reference substrate, and selecting the silicon substrate when the size of the holes or scratches is less than 6 nm in the reference substrate.

* * * * *

UNITED STATES PATENT AND TRADEMARK OFFICE
CERTIFICATE OF CORRECTION

PATENT NO. : 9,244,019 B2
APPLICATION NO. : 13/547763
DATED : January 26, 2016
INVENTOR(S) : Patrick Reynaud and Christophe Gourdel It is certified that error appears in the above-identified patent and that said Letters Patent is hereby corrected as shown below:

On the title page:
In ITEM (57) ABSTRACT:

LINE 9, change "between 1 hour and 10 hour hours" to --between 1 hour and 10 hours--

In the specification:

COLUMN 11, LINE 7, change "of the SOL The" to --of the SOI. The--

Signed and Sealed this
Twenty-eighth Day of June, 2016

Michelle K. Lee
*Director of the United States Patent and Trademark Office*